US007659324B2

(12) United States Patent
Moszner et al.

(10) Patent No.: US 7,659,324 B2
(45) Date of Patent: Feb. 9, 2010

(54) DENTAL MATERIALS WITH IMPROVED COMPATIBILITY

(75) Inventors: Norbert Moszner, Eschen (LI); Urs Karl Fischer, Arbon (CH); Peter Burtscher, Rankweil (AT); Jörg Angermann, Feldkirch (AT); Volker M. Rheinberger, Vaduz (LI)

(73) Assignee: Ivoclar Vivadent AG, Schaan (LI)

( * ) Notice: Subject to any disclaimer, the term of this patent is extended or adjusted under 35 U.S.C. 154(b) by 348 days.

(21) Appl. No.: 11/016,461

(22) Filed: Dec. 17, 2004

(65) Prior Publication Data

US 2005/0203199 A1 Sep. 15, 2005

(30) Foreign Application Priority Data

Mar. 9, 2004 (DE) ........................ 10 2004 011 497

(51) Int. Cl.
*C08F 2/50* (2006.01)
*C08J 3/28* (2006.01)
*A61K 6/00* (2006.01)
*A61K 6/08* (2006.01)
*A61K 6/083* (2006.01)

(52) U.S. Cl. ........................ 522/183; 522/35; 522/71; 522/74; 522/78; 522/81; 522/83; 522/85; 522/96; 522/90; 522/100; 522/104; 522/113; 522/114; 522/115; 522/116; 522/119; 522/120; 522/121; 522/134; 522/135; 522/136; 522/137; 522/142; 522/144; 522/150; 522/904; 522/908; 522/173; 522/174; 522/178; 522/181; 522/182; 523/109; 523/113; 523/114; 523/115; 523/116; 523/117; 523/118; 433/228.1

(58) Field of Classification Search .................. 522/35, 522/71, 74, 77, 78, 81, 83, 85, 96, 90, 100, 522/104, 113, 114, 115, 116, 119, 120, 121, 522/134, 135, 136, 137, 142, 144, 150, 153, 522/904, 908; 523/109, 113, 114, 115, 116, 523/117, 118; 433/228.1
See application file for complete search history.

(56) References Cited

U.S. PATENT DOCUMENTS

| 2,675,394 | A | | 4/1954 | Straley et al. |
| 4,639,498 | A | | 1/1987 | Ritter |
| 4,966,934 | A | | 10/1990 | Huang et al. |
| 5,081,164 | A | | 1/1992 | Lai |
| 5,180,756 | A | | 1/1993 | Rehmer et al. |
| 5,276,068 | A | | 1/1994 | Waknine |
| 5,886,064 | A | * | 3/1999 | Rheinberger et al. ........ 523/116 |
| 6,296,986 | B1 | | 10/2001 | Illsley et al. |
| 6,410,044 | B1 | | 6/2002 | Chudzik et al. |

FOREIGN PATENT DOCUMENTS

| DE | 19 31 452 | 1/1970 |
| DE | 19 33 657 | 1/1971 |
| DE | 44 16 857 C1 | 6/1995 |
| DE | 44 43 702 | 6/1996 |
| DE | 197 36 665 | 2/1999 |
| DE | 199 03 177 C2 | 7/2001 |
| EP | 0 509 516 A2 | 10/1992 |
| EP | 0 618 242 A2 | 10/1994 |
| GB | 2 280 905 A | 2/1995 |
| WO | WO 93/14147 | 7/1993 |
| WO | WO 93/17060 | 9/1993 |
| WO | WO 98/24831 | 6/1998 |
| WO | WO 01/60322 | 8/2001 |
| WO | 02/20625 A1 | 3/2002 |
| WO | 02/100453 A1 | 12/2002 |

OTHER PUBLICATIONS

Angiolini et al., "Synthesis and Photoinitiation Activity of Radical Polymeric Photoinitiators Bearing Side-Chain Camphorquinone Moieties," *Macromal. Chem. Phys.* 201:2646-2653 (2000).
Backson et al., "Synthesis and Properties of Aramid Dendrimers," *Macromal. Symp.* 77:1-10 (1994).
Bailey et al., "Polymeric Ultraviolet Absorbers," *J. Macromol. Sci.-Rev. Macromol. Chem.* C14(2):267-293 (1976).
Corrales et al., "Free Radical Macrophotoinitiators: An Overview on Recent Advances," *J. Photochem. Photobiol. A:Chem.* 159:103-114 (2003).
Cretcher et al., "The Synthesis of 5-β-Hydroxyethyl-Barbituric Acid and Its Alkyl Derivatives," *J. Amer. Chem. Soc.* 47:3083-3085 (1925).
De Feng et al., "The Role Amine in Vinyl Radical Polymerization," *Makromol. Chem., Macromol. Symp.* 63:1-18 (1992).
de Groot et al., "Hydrophilic Polymeric Acylphospine Oxide Photoinitiators/Crosslinkers for in Vivo Blue-Light Photopolymerization," Biomacromolecules 2:1271-1278 (2001).
Dnebosky et al., "Polymerizable Amines as Promoters of Cold-Curing Resins and Composites," *J. Dent. Res.* 54:772-776 (1975).
Kamogawa et al., "Synthesis of Polymerizable p-Styrene Sulfinate," *Chem. Letters* pp. 419-420 (1976).
Li et al., "Copolymerization of 4,4'-Divinyl Benzoyl Peroxide with Methyl Methacylate and Grafting of Butyl Acrylates onto the Copolymers," *Macromol. Rapid Commun.* 21:590-594 (2000).
Mizyuk et al., "α, α-Dialkoxyaryl Ketones and Related Compounds I. Reaction of Phenylglyoxal with Primary Alcohols in an Acidic Medium," *Russian Journal of Org. Chem.* 30(4):570-577 (1994).
Moszner et al., "Synthesis and Hydrolytic Condensation of New Cross-Linking Alkoxysilane Methacrylates and Light-Curing Composites Based upon the Condensates," *Macromol. Mat. Eng.* 287:339-347 (2002).
Ono et al., "A Convenient Procedure for Esterification of Carboxylic Acids," *Bull. Chem. Soc. Jpn.* 51(8):2401-2404 (1978).
Padias et al., "Starburst Polyether and Polythioether Dendrimers," *Polym. Prepr. Am. Chem. Soc., Div. Polym. Chem.* 30:119-120 (1989).

(Continued)

*Primary Examiner*—Sanza L McClendon
(74) *Attorney, Agent, or Firm*—Nixon Peabody LLP

(57) ABSTRACT

Dental materials which contain a radically polymerizable organic binder, at least one radical polymerization initiator and at least one radical polymerization accelerator, both the initiator and the accelerator each having at least one radically polymerizable group.

23 Claims, No Drawings

OTHER PUBLICATIONS

Tanzi et al., "Physical Characterization of Acrylic Bone Cement Cured with New Accelerator Systems," *Clinical Materials* 8:131-136 (1991).

Vazquez et al., "Role of Amine Activators on the Curing Parameters, Properties and Toxicity of Acrylic Bone Cements," *Polym. Intern.* 46:241-250 (1998).

Weiwei et al., "Convenient Syntheses of 2-Alkyl(Aryl)-4,5-diphenyloxazoles and 2-Alkyl(Aryl)-4-phenyloxazoles," *Synthesis* pp. 1298-1304 (1998).

Wooley et al., "One-Step Synthesis of Hyperbranched Polyesters. Molecular Weight Control and Chain End Functionalization," *Polymer Journal* 26:187-197 (1994).

* cited by examiner

DENTAL MATERIALS WITH IMPROVED COMPATIBILITY

The invention relates to dental materials which are characterized by an improved body compatibility.

Dental materials based on organic resins usually represent complex mixtures of different components which, besides polymerizable monomers and/or oligomers, contain at least one initiator for radical polymerization and in most cases also contain further components such as polymerization accelerators, inhibitors and/or UV stabilizers. These are often compounds of low molecular weight which are problematical from a toxicological point of view. During curing most of the monomers used are covalently bound into the forming polymer network and thus prevented from diffusing into the surrounding tissue. The remaining components are however only physically enmeshed in the polymer network and can therefore, in the course of time, be washed out of the dental material, which is undesirable from the point of view of tissue compatibility.

Li et al., Macromol. Rapid Commun. 21 (2000) 590-594, describe the copolymerization of 4,4'-divinylbenzoyl peroxide with methyl methacrylate and the grafting of butyl acrylates onto the copolymers.

Dnebosky et al., J. Dent. Res. 54 (1975) 772-776, describe N,N-substituted aminoethyl methacrylates which are suitable as accelerators for the benzoylperoxide-catalyzed polymerization of methyl methacrylate. These aminoethyl methacrylates are incorporated into the polymer chains, the aim being to thereby reduce the toxicity of filling composites.

Tanzi et al., Clinical Materials 8 (1991) 131-136, disclose two unsaturated, tertiary arylamines, i.e. N-acryloyl- and methacryloyl-N'-phenylpiperazine, which are to be chemically bound into the polymer network during the radical benzoylperoxide catalyzed polymerization.

The chemical compound 2-(2'-hydroxy-5'-methacryloxyethylphenyl)-2H-benzotriazole which is said to be suitable as a copolymerizable UV-absorber e.g. for the production of contact lenses is marketed by Ciba Specialty Chemicals under the name Ciba® Tinuvin® R 796.

From DE OS 19 31 452 polymeric antioxidants for plastics are known which are based on monomers with sterically hindered phenol groups.

DE OS 19 33 657 discloses acryloyloxyphenols and polymerisates thereof which are suitable as anti-oxidants in particular for textiles.

U.S. Pat. No. 5,276,068 relates to dental materials which contain polycarbonate-dimethacrylate condensation products as chief component. These are combined with conventional monomers, initiators, antioxidants and other additives. Dimethylaminoethyl methacrylate and diethylaminoethyl methacrylate inter alia are named as suitable polymerization accelerators for photopolymerization.

Angiolini et al., Macromal. Chem. Phys. 201 (2000) 2646, have synthesized polymeric photoinitiators and amine accelerators and examined their polymerization behaviour. The use of one polymeric component led to a delay in the polymerization; when both polymeric components were used, a distinct reduction in the polymerization rate was determined, which is attributed to steric hindrances. The polymerizations were carried out in benzene as solvent.

Known materials always contain a lesser or greater proportion of components which are not covalently bound into the polymer network during the curing of the materials. After the curing of the materials these components can migrate into neighbouring body tissue and trigger toxic reactions there.

The object of the invention is to provide dental materials which can be cured by means of polymerization and which after curing contain a minimum amount of components which could diffuse into neighbouring tissue and trigger undesired secondary reactions.

This object is achieved by materials which contain a radically polymerizable organic binder, at least one initiator for the radical polymerization and at least one accelerator for the radical polymerization. The materials are characterized in that both initiator and accelerator each have at least one radically polymerizable group.

It was found that these substances can be cured without problems by radical polymerization, materials being obtained which contain an extremely small proportion of soluble components. This result is surprising inasmuch as the state of the art suggests a distinct reduction in the polymerization rate when using initiators and accelerators with polymerizable groups, as both components are incorporated into the polymer network, which reduces the probability of reaction through steric and kinetic effects (Angiolini, loc. cit.). The joint use of a polymerizable initiator and a polymerizable accelerator for the radical polymerization of dental materials has not been described until now.

Monomers and oligomers with radically polymerizable groups are used as organic binders. By radically polymerizable groups are meant herein preferably ethylenically unsaturated groups and in particular (meth)acryl, allyl, styryl, vinyl, vinyloxy and/or vinylamine groups. According to the invention all binders which can be used for a dental material are suitable, in particular monomers and oligomers which have at least one ethylenically unsaturated group. Such monomers and oligomers can be used alone or in mixture. Preferably the binder contains at least one polyfunctional monomer or oligomer, i.e. a monomer or oligomer with two or more, preferably three or more and quite particularly preferably four or more polymerizable ethylenically unsaturated groups. Monomers and oligomers with two or more radically polymerizable groups act as crosslinking agents during the polymerization. Monomers or oligomers with only one radically polymerizable group are called monofunctional monomers or oligomers.

Polysiloxanes with polymerizable ethylenically unsaturated groups are particularly suitable as crosslinking agents and in particular (meth)acrylate-modified polysiloxanes which are accessible by hydrolytic condensation e.g. of corresponding (meth)acrylate-group-containing silanes. Particularly preferred are condensates which contain no non-functionalized silane units, i.e. polysiloxanes in which each siloxane-repetition unit has at least one, preferably two or three polymerizable ethylenically unsaturated groups. These polysiloxanes are characterized by a high functionality, i.e. a high number of polymerizable groups. Because of the high functionality a practically complete incorporation of the polysiloxanes into the cured dental material takes place. In addition, the polysiloxanes are also characterized by a low solubility in water or aqueous solutions, so that even very small non-polymerized proportions are not soluble out of the dental material under oral conditions, and therefore cannot be washed out either.

(Meth)acryl silanes suitable for the production of the polymerizable polysiloxanes are commercially available, such as e.g. 3-(Methacryloyloxy)propyltrimethoxysilane (MEMO), or can be easily produced e.g. by reaction of glycerine dimethacrylate with 3-isocyanatopropyltriethoxysilane (DMAURS, EP 0 618 242 A2) or

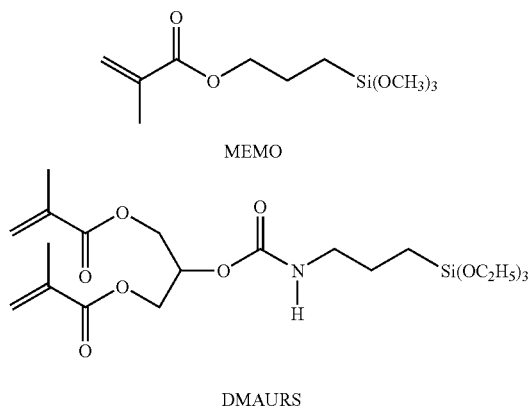

MEMO

DMAURS 3-(Methyldiethoxysilyl)-propyl succinic acid anhydride (DMBES, DE 44 16 857 C1) or with glutaric acid anhydride followed by reaction with 3-aminopropyltriethoxysilane (DMAGAMS, DE 199 03 177 C2), the production of the (meth)acrylate-modified polysiloxanes by hydrolytic condensation of the (meth)acrylate-group-containing silanes also being described in the named publications.

Also advantageous, especially for composites, are the methacrylate-group-containing polysiloxanes described in DE 199 03 177 C2 which are produced from siloxanes in which the hydrolytically condensable trialkoxysilyl group is connected to the polymerizable methacrylate groups via a flexible aminoalkyl group (e.g. DMAMS), as the corresponding polysiloxanes PK-DMAMS are characterized by a comparatively low viscosity. In the case of composites a high degree of filling can thus be achieved.

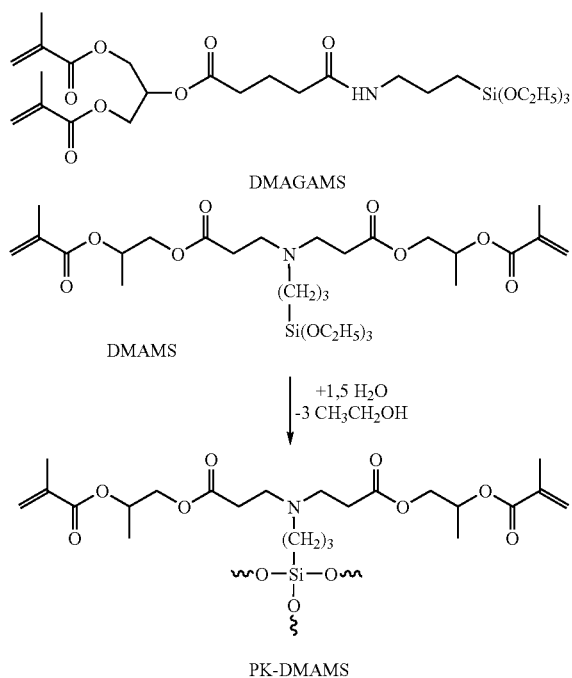

DMAGAMS

DMAMS

PK-DMAMS

Further preferred binders are hyperbranched polymers modified with ethylenically unsaturated groups, so-called dendrimers.

Dendrimers are three-dimensional, high order oligomeric and polymeric compounds which are synthesized starting from small initiator-molecules by a constantly repeating reaction sequence (cf. DE 44 43 702).

Dendrimers preferred according to the invention (propylenimine dendrimers) are obtained by reaction of hydroxyl or amino-group-containing initiator molecules with vinyl cyanides, such as for example acrylo- or methacrylonitrile. Suitable propylenimine dendrimers and processes for producing them are described in WO93/14147. Further groups of preferred dendrimers are the polyether/polythioether (A. B. Padias et al.; Polym. Prepr. Am. Chem. Soc., Div. Polym. Chem. 30 (1989) 119), polyester (WO93/17060), polyphenylene amide (S. C. E. Backson et al.; Macromol. Symp. 77 (1994) 1) and polyphenylene ester dendrimers (K. L. Wooley et al., Polymer Journal 26 (1994) 187). Dendrimers which have a spherical structure are particularly preferred. In addition dendrimers of the 4th or a higher generation are particularly suitable according to the invention.

The dendrimers have preferably ethylenically unsaturated end-groups. The reactive groups of the last generation of reactants are called end-groups. The synthesis of dendrimers with polymerizable end-groups takes place by the reactions, known from organic chemistry, of the abovementioned dendrimers with suitable monomer reagents. Particularly suitable raw materials are dendrimers with carboxyl, hydroxyl and/or amino end-groups. Methacrylic acid chloride and isocyanatoethyl methacrylate are preferred for the reaction of hydroxy- or amino-functionalized dendrimers and 2-hydroxyethylmethacrylate for the reaction of carboxyl-group-containing dendrimers. For the reaction of amino-group-containing dendrimers the Michael reaction with acryloyloxyethyl methacrylate (AEMA) is particularly preferred. The Michael reaction takes place selectively at the acrylate double bond, whilst the methacrylate double bond is retained as a polymerizable group. Such dendrimers and their production are disclosed in DE 44 43 702.

A further group of suitable polymerizable dendrimers according to the invention are epoxide amine dendrimers which contain a core molecule with at least one primary amino group, at least one thiol group, at least one phenol group, at least one carboxylic acid group or at least two secondary amine groups or with a combination of these groups and a branching molecule. Such dendrimers and their production are disclosed in WO 98/24831.

In addition, according to the invention silane dendrimers with terminal alkenyl groups are preferred, as are described in DE 197 36 665. Mixtures of the named dendrimers are also suitable.

The abovementioned polysiloxanes and dendrimers are characterized in that they contain a large number of polymerizable, ethylenically unsaturated groups per molecule and can therefore be polymerized with high monomer conversion.

Quite preferred polysiloxanes are polycondensates which are accessible by hydrolytic polycondensation of one or more of the following silanes: bis[2-(2-(methacryloyl oxyethoxycarbonyl)ethyl)]-3-triethoxysilylpropyl amine, bis[2-(2(1)-(methacryloyloxypropoxycarbonyl)ethyl)]-3-triethoxysilylpropyl amine, 1,3(2)-dimethacryloyloxypropyl-[3-(3-triethoxysilylpropyl)aminocarbonyl]propionate, 1,3(2)-dimethacryloyloxypropyl-[4-(3-triethoxysilylpropyl) aminocarbonyl]butyrate, 1,3(2)-dimethacryloyloxypropyl-[4-(3-triethoxysilylpropyl)-N-methylaminocarbonyl] butyrate, 3-[1,3(2)-dimethacryloyl oxypropyl)-2(3)-oxycarbonyl amido]-propyltriethoxysilane.

Quite particularly preferred dendrimers are polypropylenimine, epoxidaminie and silane dendrimers which have at least 4 terminal polymerizable groups, preferably vinyl and/or (meth)acryl groups.

Further preferred binders are radically polymerizable crosslinking monomers, such as the known multifunctional acrylates and/or methacrylates, e.g. bisphenol-A-di(meth)acrylate, bis-GMA (an addition product of methacrylic acid and bisphenol-A-diglycidyl ether), UDMA (an addition product of 2-hydroxyethyl methacrylate and 2,2,4-trimethylhexamethylene diisocyanate), di-, tri- or tetraethylene glycol di(meth)acrylate, trimethylolpropanetri(meth)acrylate, pentaerythritol tetra(meth)acrylate, and butanediol di(meth)acrylate, 1,10-decanediol di(meth)acrylate or 1,12-dodecanediol di(meth)acrylate.

According to the invention binders are preferred which contain exclusively radically polymerizable monomers and/or oligomers with two or more ethylenically unsaturated groups. According to a particularly preferred version, binders are used which contain at least one radically polymerizable polysiloxane and/or ethylenically unsaturated dendrimer, quite particularly preferred are those which contain exclusively one or more radically polymerizable polysiloxanes and/or ethylenically unsaturated dendrimers.

As initiators for the radical polymerization, according to the invention one or more initiators are used which contain at least one radically polymerizable group per initiator molecule.

As initiators, alpha-diketones, azo compounds, peroxides, benzile dimethyl ketals, benzoin ethers, dialkoxyacetophenones and trimethyl benzoyl phosphine oxides with ethylenically unsaturated groups are particularly suitable. Compounds which contain a photoinitiator are preferred.

Preferred photoinitiators are polymerizable camphorquinone derivatives, such as for example 10-methacryloyl oxycamphorquinone (MACQ), which can be obtained by reaction of 10-hydroxycamphorquinone with methacrylic acid chloride (L. Angiolini, 2000, Macromol. Chem. Phys., 201, 2646).

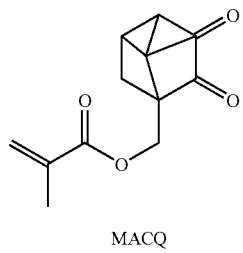

MACQ

Such camphorquinone derivatives are preferably combined with amines as accelerators.

Peroxides and azo compounds are particularly suitable as thermal initiators. A preferred polymerizable peroxide is for example 4,4'-divinylbenzoyl peroxide (DVBPO), which is accessible by reaction of 4-vinyl benzoyl chloride with sodium peroxide (Z. Li et al., 2000, Macromol. Rapid Commun., 590-594). A preferred polymerizable azo compound is the ester of 2-hydroxyethyl methacrylate and 4,4'-azobis-(4-cyanovalerianic acid) ACVMA:

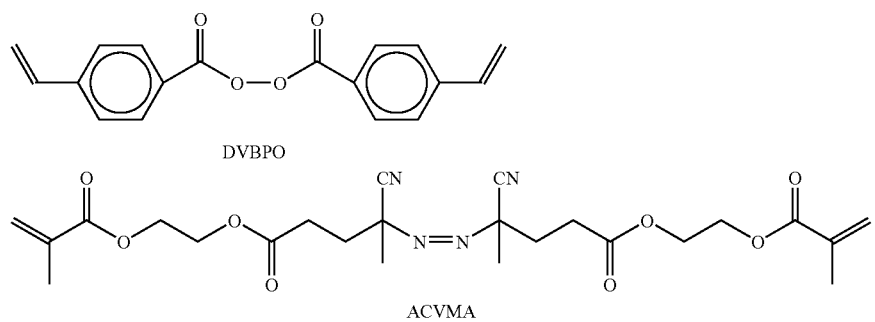

Such azo compounds can be obtained by reacting suitably functionalized commercial azo compounds, such as e.g. azo bis(4-cyanovaleric acid), with suitably functionalized polymerizable compounds, in the case of the azocarboxylic acids e.g. with 2-hydroxyethyl methacrylate in the presence of a condensation agent, such as dicyclohexylcarbodiimide, or with 2-isocyanatoethyl methacrylate in the presence of a tin catalyst.

Preferred polymerizable UV initiators are derived from acyl phosphine oxides (APOs), dialkoxyacetophenones or benzoin derivatives. Examples of polymerizable UV initiators are the styrene derivative SAPO (J. H. de Groot et al., 2001, Biomacromolecules, 2 1271), the bis-allyl compound DAA (V. L. Mizyuk, et al., 1994, Org. Chem. 30/4, 570) or the acrylate BA (P. Weiwei et al., 1998, Synthesis, 1298). Further examples of monomeric photoinitiators/sensitizers are included in a review by T. Corrales et al. (J. Photochem. Photobiol. A: Chem. 159 (2003) 103).

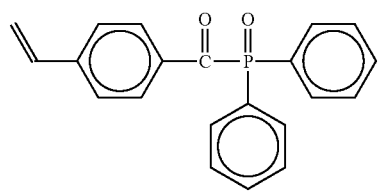

SAPO

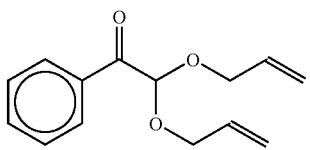

DAA

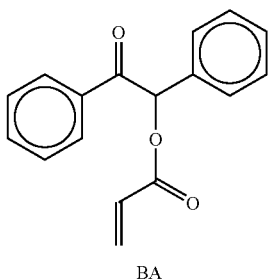

BA

Reduction agents are used, preferably amines, as polymerizable accelerators for the radical polymerization. Preferred polymerizable amines are N-(2-methacryloyloxyethyl)-N-methylaniline (MAAMA), N-(2-methacryloyloxyethyl)-N-methyl-3,5-xylidine (MAMA3,5X), N-(2-methacryloyloxyethyl)-N-methyl-p-toluidine (MAAMpT), N,N-bis-(2-methacryloyloxyethyl)-p-toluidine (DMAApT) and N,N-bis-(2-methacryloyloxyethyl)-3,5-xylidine (DMAA3,5X) (J. Dnebosky et al., 1975, J. Dent. Res. 54, 772-776).

Further preferred polymerizable amines which are suitable as accelerators for radical polymerization are the commercially available 2-(dimethylamino)ethylmethacrylate (DMAEMA), N-(2-methacryloxyethyl)-N'-methyl piperazine (MAMP) or N-(methacrylamidomethyl)morpholine (MAMMM) (B. Vazquez, B. Levenfeld, J. San Roman, Polym. Intern. 1998, Role of amine activators on the curing parameters, properties and toxicity of acrylic bone cements, 46, 241-250, X. De Feng, Makromol. Chem., Macromol. Symp. 1992, The role of amine in vinyl radical polymerization, 63, 1-18).

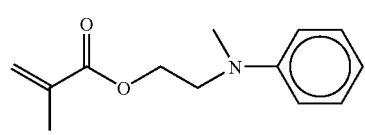

MAAMA

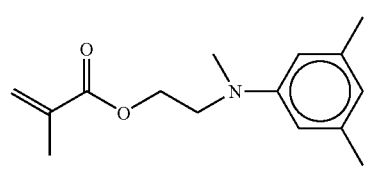

MAMA3,5X

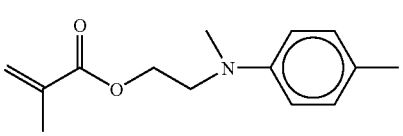

MAAMpT

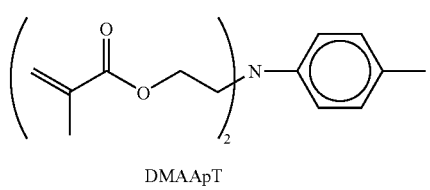

DMAApT

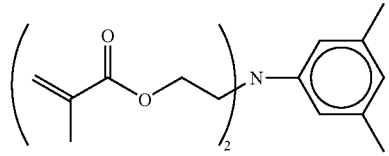

DMAA3,5X

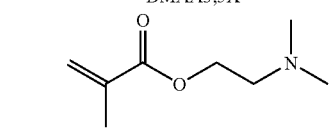

DMAEMA

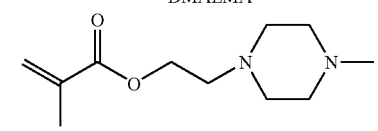

MAMP

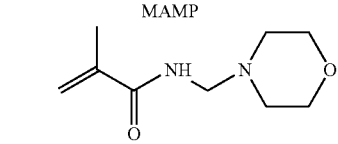

MAMMM

If the amine accelerators are used in combination with peroxides, cold-curing materials are obtained.

Barbituric acid and sulphinic acid derivatives are useful as accelerators in redox systems. Examples of polymerizable derivatives are the compounds VOBA (L. H. Cretscher et al., 1925, J. Amer. Chem. Soc. 47, 3083-3085) or SSA (H. Kamogawa et al., 1976, Chem. Letters, 419-420):

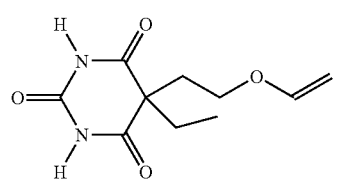

VOBA

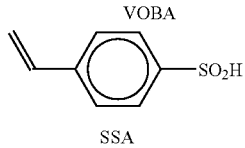

SSA

In addition to the named components the dental materials according to the invention preferably also contain at least one polymerizable UV absorber, i.e. a UV absorber which has at least one radically polymerizable group. UV stabilizers serve to improve the colour stability of the materials and prevent e.g. yellowing upon exposure to ultraviolet light, by absorbing the high-energy UV radiation and converting it into heat or deactivating high-energy states. Suitable polymerizable UV absorbers are described for example in D. Bailey et al., 1976, J. Macromol. Sci.-Rev. Macromol. Chem. C14, 267-293. Preferred polymerizable UV absorbers are hydroxyphenyl benzotriazoles, such as for example 2-(2'-hydroxy-5'-methacryloyloxyethylphenyl-2-benzotriazole (HMAEPBT), which is commercially available from Ciba Specialty Chemicals under the name Tinuvin® R796.

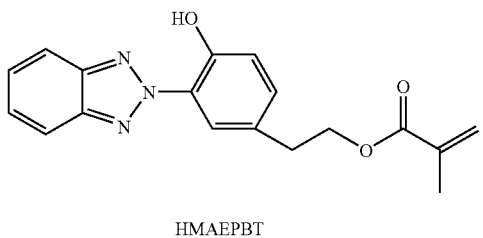

HMAEPBT

In addition the materials according to the invention preferably also contain at least one radically polymerizable inhibitor. Inhibitors prevent premature spontaneous polymerization, are therefore also called stabilizers and make possible a storage stability of approximately 2 years. A distinction is drawn between aerobic inhibitors, which are effective only in the presence of oxygen, and anaerobic inhibitors, which are also effective in the absence of oxygen. In the case of self-curing systems inhibitors additionally guarantee an adequate processing time. During this so-called inhibition period the inhibitors form inactive products with the radicals formed from the initiator or oligomeric growth radicals. Only when the inhibitor is used up does the actual curing phase begin.

Polymerizable phenol derivatives are preferred as aerobic inhibitors. Particularly preferred examples of these are 4-hydroxyphenyl acrylate (HPhA) (U.S. Pat. No. 2,675,394) and 4-methacryloyloxy-2,6-di-tert.-butylphenol (MADtBPh) (DE 19 33 657).

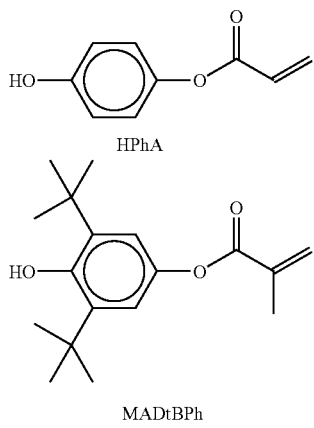

Preferred anaerobic inhibitors are polymerizable (meth) acrylate derivatives of 2,2,6,6-tetramethyl-piperidine-1-oxyl-radical (TEMPO), such as for example N,N-bis-(2-hydroxy-3-methacryloyloxypropoxy)-4-amino-2,2,6,6,-tetramethyl-piperidine-1-oxyl radical (BMAP-TEMPO) or N,N-bis-(3-oxa-4-oxo-6-methacryloyloxyhexyl)-4-amino-2,2,6,6,-tetramethylpiperidine-1-oxyl radical (BMAH-TEMPO) (WO 01/60322):

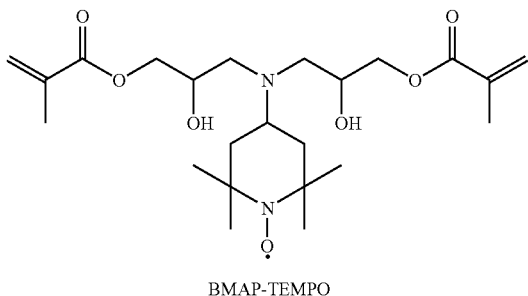

BMAP-TEMPO

According to the invention, dental materials are particularly preferred which contain exclusively radically polymerizable components, i.e. initiators, accelerators, optionally UV stabilizers, optionally inhibitors, which can be bound into the polymer network during the polymerization. The proportion of low-molecular-weight constituents which could be washed out after curing or diffuse into the surrounding tissue is thereby reduced to a minimum. Materials which contain no non-radically polymerizable monomeric or polymeric constituents are particularly preferred. Also preferred are compounds which contain no solvent. By solvent is meant here substances liquid at room temperature which serve only to control the reaction or to facilitate handling, without still being present or necessary in the finished cured composition. Liquid monomers are therefore not solvents in this sense.

In addition to the named constituents, the dental materials according to the invention can preferably also contain fillers which serve to improve the mechanical properties,. Organic or inorganic particles or fibres are suitable for this purpose. Preferred inorganic particulate fillers are amorphous, spherical materials based on oxides, such as $ZrO_2$ and $TiO_2$ or mixed oxides of SiO2, $ZrO_2$ and/or $TiO_2$, nanoparticulate or microfine fillers, such as pyrogenic silicic acid or precipitated silicic acid as well as macro- or minifillers, such as quartz, glass ceramics or glass powder with an average particle size of 0.01 to 5 μm as well as X-ray-opaque fillers, such as ytterbium trifluoride. In addition, glass fibres, polyamide or carbon fibres can also be used.

Depending on the type of fillers and the use, the maximum degree of filling preferably lies between 50 and 90 wt.-%, particularly preferably 55-85 wt.-%. Composites, i.e. filler-containing dental materials, are subdivided according to the particle size and composition of the fillers into macrofiller composites, homogeneous and heterogeneous microfiller composites and hybrid composites. Macrofillers are preferably produced by grinding quartz, X-ray-opaque glasses, borosilicates or ceramics, are purely inorganic in nature and consist in most cases of chip-shaped parts with an average particle size of approximately 0.4 to 10 μm. As micro fillers, pyrogenic $SiO_2$ or precipitated silicic acid are preferably used, sometimes also mixed oxides, e.g. $SiO_2$—$ZrO_2$, which are accessible by hydrolytic co-condensation of metal alkoxides (e.g. tetraethoxysilane or tetrapropyl zirconate). The microfillers have an average particle size of approximately 5 to 100 nm and, because of their large specific surface of 40 to 300 $m^2/g$, exhibit a strong viscosity-increasing effect. Heterogeneous microfiller composites contain so-called microfiller complexes. Examples of this are chip-shaped pre-polymerized micro-filled complexes, which are accessible e.g. by working pyrogenic $SiO_2$ into a resin matrix, followed by thermal curing of the mixture and grinding of the filled polymerisate. According to the invention, fillers which contain no soluble components are preferred.

The fillers are preferably surface-modified with an adhesion promoter before being worked into the binder. Adhesion promoters which have at least one radically polymerizable group are preferred. Particularly preferred adhesion promoters are silanes, in particular alpha- and gamma-methacryloyloxypropyltrimethoxysilane. Materials which contain at least 3 wt.-% of filler are preferred.

In addition the compositions used according to the invention contain further additives, such as e.g. colorants (pigments) or polymerizable, microbiocidal materials. Pigments are added to establish the intrinsic colour or transparency. Inorganic pigments are preferred, especially mixed-phase pigments based on metal oxides, e.g. $TiO_2$ rutile with substitution of titanium ions by chromium/antimony (yellow) or replacement of the metal ions in the MgAl$_2$O$_4$ spinel by cobalt (blue) or copper (black). As such pigments are insoluble, they will not, as a rule, adversely affect the biocompatibility of the dental material.

Preferred dental materials according to the invention contain, apart from fillers and pigments, exclusively components which have ethylenically unsaturated groups and are thus bound into the polymer network during the polymerization. Fillers and pigments are as a rule insoluble and are therefore not leached out of the polymer. In order to improve the mechanical properties, the fillers are however preferably treated with adhesion promoters which have ethylenically unsaturated groups, so that these are also integrated into the polymer.

Particularly preferred are dental materials which contain:
(a) 1 to 50 wt.-%, in particular 5 to 40 wt.-% of binder, preferably binder with two or more polymerizable groups per binder molecule,
(b) 0.1 to 5.0 wt.-%. in particular 0.2 to 2.0 wt.-% of radically polymerizable initiator,
(c) 0.1 to 5.0 wt.-%, in particular 0.2 to 2.0 wt.-% of radically polymerizable accelerator, and optionally
(d) 0.01 to 3.0 wt.-%, in particular 0.05 to 2.0 wt.-% inhibitor, preferably radically polymerizable inhibitor,
(e) 0 to 90, in particular 3 to 80 wt.-% of filler.

All data relate in each case to the total mass of the material.

The materials according to the invention are characterized in that they, compared with conventional materials, contain only a very small proportion of soluble components, but in spite of this can be cured within a comparable time. This is surprising as, in the light of the results published by Angiolini et al. loc. cit., a clearly reduced polymerization rate was to be expected, all the more so as the compositions according to the invention, according to a preferred version, are not polymerized in a solution, whereby the steric hindrances found by Angiolini et al. should be further intensified.

The dental materials according to the invention are particularly suitable as filling materials, fixing cements and dental coating materials. In addition the materials are highly suitable for the production of artificial teeth, dental prostheses, inlays and facing materials. Dental materials for intraoral applications are preferred.

The invention is explained in more detail below with reference to examples.

EMBODIMENTS

EXAMPLE 1

Synthesis of the dimethacrylate-group-containing polysiloxane OM-51

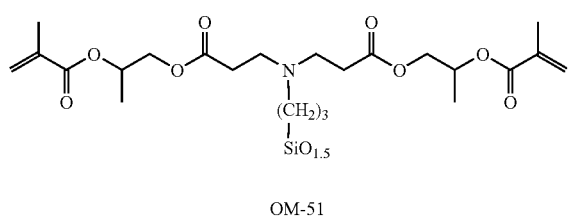

OM-51

260 mmol (160.6 g) of the silane bis-[[methacryloyloxy) propoxycarbonylethyl]-[triethoxysilylpropyl]-amine, which was produced according to the literature (N. Moszner, et al., 2002, Macromol. Mat. Eng., 287 339-347), was dissolved in 380 ml of EtOH. The hydrolysis of the silane took place by addition of water in the form of a 0.1 N NH$_4$F solution (28.1 g). After 24 hours' stirring at room temperature the volatile components were removed under vacuum with the introduction of some air. The resultant viscous resin (approximately 120 g of OM-51) showed a viscosity η of 8 Pas (23° C.).

EXAMPLE 2

Synthesis of the polymerizable amine accelerator EMBO-MA

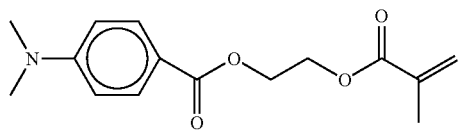

EMBO-MA

Analogously to N. Ono et al., 1978, Bull. Chem. Soc. Jpn., 51, 2401, 0.10 mol (20.0 g) of 2-bromoethyl methacrylate was slowly added dropwise to a solution of 0.10 mol (17.1 g) of 4-dimethylaminobenzoic acid and 0.10 mol (15.8 g) of 1,8-diazabicyclo[5.4.0]undec-7-ene in 240 ml of toluene, and heated under reflux for 16 h. The reaction solution was washed with 1.0 N NaOH solution, with 1.0 N hydrochloric acid and finally with water. The organic phase was then dried over anhydrous Na$_2$SO$_4$, concentrated in a rotary evaporator and left to crystallize out overnight. 13.0 g (45.3% of theory) of white crystals of 2-(methacryloyloxyethyl)-4-dimethylaminobenzoate (EMBO-MA) was obtained.

EXAMPLE 3

Synthesis of a polymerizable camphorquinone methacrylate MACQ

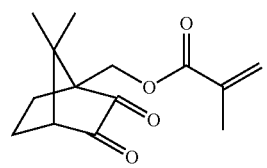

MACQ

Analogously to L. Angiolini et al., 2000, Macromol. Chem. Phys. 201, 2646, a mixture of 10 mmol (1.82 g) of 10-hydroxycamphorquinone, 10 mg of 2,6-di-tert.butyl-4-methylphenol (inhibitor), 1.5 ml of dry triethylamine (TEA) and 50 ml of absolute 1,4-dioxane, under argon and with exclusion of daylight, was added dropwise at 0° C. to a stirred solution of 11 mmol (1.15 g) of methacrylic acid chloride, dissolved in 20 ml of 1,4-dioxane. There followed stirring for 2 h at room temperature and 2 h under reflux. The reaction mixture was filtered off from the formed TEA-HCl, diluted with diethyl ether, washed with 5% sodium bicarbonate solution and with water. After drying over anhydrous Na$_2$SO$_4$ the solution was concentrated to dryness in a rotary evaporator and the solid crude product recrystallized from toluene/n-hexane (20:80 v/v). 1.55 g (62% of the theory) of yellow crystals of 10-methacryloyloxycamphorquinone MACQ was obtained.

EXAMPLE 4

Synthesis of the polymerizable inhibitor MA-HQ

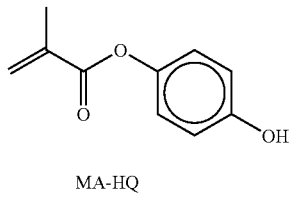

MA-HQ

Analogously to DE 193 36 57, 140 mmol (21.0 g) of methacrylic acid anhydride were added at a temperature <25° C. to 145 mmol (16.0 g) of freshly recrystallized hydroquinone, dissolved in 150 ml of anhydrous tetrahydrofuran under argon followed by 1.0 ml of 96% sulphuric acid. The reaction mixture was stirred for 16 h at room temperature. The mixture was poured into 800 ml of water, neutralized with 2 N sodium hydroxide solution, stirred for 2 h and the solid crude product was removed by suction. The product was then recrystallized from n-hexane several times and 9.17 g (37% of the theory) of white crystals of hydroquinone monomethacrylate MA-HQ was obtained.

EXAMPLE 5

Composite based on polymerizable matrix components

A mixture of the monomer components listed below was produced. This was then processed in a planetary kneader (Linde) with the filler to produce a homogeneous composition.

Composition of the monomer mixture

| Component | Proportion |
|---|---|
| Polysiloxane OM51 | 49.26 wt.-% |
| Urethane dimethacrylate UDMA | 49.25 wt.-% |
| Polymerizable camphorquinone MACQ | 0.50 wt.-% |
| Polymerizable amine EMBO-MA | 0.85 wt.-% |
| Polymerizable inhibitor MA-HQ | 0.14 wt.-% |

Composition of the composite paste

| Components | Proportion |
|---|---|
| Monomer mixture | 22.12 wt.-% |
| Filler mixture[a] | 77.88 wt.-% |

[a]Barium glass 1.0 μm, silanized with methacryloyloxypropyltrimethoxysilane (67.88 wt.-%), Spherosil (14.42 wt.-%), silanized with methacryloyloxypropyltrimethoxysilane (4.42 wt.-%), ytterbium fluoride $YbF_3$ (13.28 wt.-%)

From the composite paste, testpieces were prepared (disks: height 2 mm, diameter: 10 mm) with an irradiation time of 2 times 3 minutes with a Spectramat (Ivoclar Vivadent AG). The testpieces were then exhaustively extracted with ethanol for 3 days at 37° C. In the extracts, the proportion of non-converted soluble components was determined by high-pressure liquid chromatography (HPLC). The quantitative determination was carried out by evaluation of the integration of the respective peak areas. The results are shown in Table 1.

EXAMPLE 6

Composite based on non-polymerizable matrix components (comparison)

Analogously to Example 5 a mixture of the monomer components listed below was produced. This was then processed in a planetary kneader (Linde) with the filler to produce a homogeneous composition.

Composition of the monomer mixture

| Component | Proportion |
|---|---|
| Dimethacrylate TEGDMA | 15.00 wt.-% |
| Dimethacrylate bis-GMA | 35.00 wt.-% |
| Urethane dimethacrylate UDMA | 48.97 wt.-% |
| Camphorquinone CQ | 0.33 wt.-% |
| Accelerator EMBO | 0.60 wt.-% |
| Inhibitor MEHQ | 0.10 wt.-% |

Composition of the composite paste

| Component | Proportion |
|---|---|
| Monomer mixture | 22.12 wt.-% |
| Filler mixture[a] | 77.88 wt.-% |

[a]composition of the filler mixture - see Example 5

Testpieces were prepared in the manner described in Example 5 from the composite paste and exhaustively extracted with ethanol. The same molar quantities of inhibitor, accelerator and initiator were used as in Example 5. Table 1 shows the result of analysis of the extracts (non-polymerized soluble components).

TABLE 1

Proportion of soluble components in the testpieces

| Component | Example 5 [%][a] | Example 6 (comparison) [%][a] |
|---|---|---|
| Monomer | 0.9 | 5.97 |
| Photoinitiator | 0.01 | 0.4 |
| Amine accelerator | 1.2 | 17.5 |
| Inhibitor | 2.2 | 33.5 |

[a]% soluble proportions relative to the quantity used

Table 1 shows that when using matrix materials based on polymerizable organic components in a dental material given identical curing conditions, the proportion of soluble constituents can be clearly reduced, which has a favourable effect on the biocompatibility of the material.

The invention claimed is:

1. Dental material comprising a radically polymerizable organic binder, at least one initiator for the radical polymerization and at least one accelerator for the radical polymerization, wherein both initiator and accelerator each have at least one radically polymerizable group.

2. Dental material according to claim 1, in which the binder contains monomers and/or oligomers with two or more radically polymerizable groups.

3. Dental material according to claim 2, in which the binder contains at least one polysiloxane with radically polymerizable groups.

4. Dental material according to claim 2, in which the binder contains at least one dendrimer which has radically polymerizable groups.

5. Dental material according to claim 2, in which the binder contains at least one radically polymerizable crossliniking monomer.

6. Dental material according to claim 2, in which the binder contains exclusively radically polymerizable monomers and/or oligomers with two or more radically polymerizable groups.

7. Dental material according to claim 1, which contains a photoinitiator.

8. Dental material according to claim 1, which contains as initiator at least one alpha-diketone, one azo compound, one peroxide, one benzildimethylketal, one benzoin ether, one dialkoxyacetophenone and/or one trimethylbenzoyl phosphine oxide.

9. Dental material according to claim 1, which contains as accelerator an amine, a barbituric acid derivative or a sulfinic acid derivative.

10. Dental material according to claim 1, which additionally contains at least one UV absorber which has at least one radically polymerizable group.

11. Dental material according to claim 1, which additionally contains at least one inhibitor for the radical polymerization which has at least one radically polymerizable group.

12. Dental material according to claim 1, which additionally contains an anti-oxidant which has at least one radically polymerizable group.

13. Dental material according to claim 1, which contains a UV stabilizer and an inhibitor which both have one radically polymerizable group.

14. Dental material according to claim 1, which contains no non-radically polymerizable monomeric or polymeric constituents.

15. Dental material according to claim 1, which contains no solvent.

16. Dental material according to claim 1, which additionally contains filler.

17. Dental material according to claim 16, in which the filler is surface-modified with an adhesion promoter.

18. Dental material according to claim 17, in which the adhesion promoter has at least one radically polymerizable group.

19. Dental material according to claim 1, which additionally contains one or more pigments.

20. Dental material according to claim 19, which, apart from pigments and filler, contains exclusively components which have radically polymerizable groups.

21. Dental material according to claim 1, which contains
(a) 1 to 50 wt.-%, in particular 5 to 40 wt.-% of binder,
(b) 0.1 to 5.0 wt.-%, in particular 0.2 to 2.0 wt.-% of initiator,
(c) 0.1 to 5.0 wt.-%, in particular 0.2 to 2.0 wt.-% of accelerator in each case relative to the total mass of the material.

22. Dental material according to claim 21, which additionally contains (d) 0.01 to 3.0 wt.-%, in particular 0.05 to 2.0 wt.-% of inhibitor, relative to the total mass of the material.

23. Dental material according to claim 21, which additionally contains (e) 0 to 90, in particular 3 to 80 wt.-% of filler, relative to the total mass of the material.

* * * * *

UNITED STATES PATENT AND TRADEMARK OFFICE
CERTIFICATE OF CORRECTION

| | |
|---|---|
| PATENT NO. | : 7,659,324 B2 |
| APPLICATION NO. | : 11/016461 |
| DATED | : February 9, 2010 |
| INVENTOR(S) | : Moszner et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 429 days.

Signed and Sealed this

Thirtieth Day of November, 2010

David J. Kappos
*Director of the United States Patent and Trademark Office*